United States Patent
Milnes et al.

(10) Patent No.: US 12,011,389 B2
(45) Date of Patent: Jun. 18, 2024

(54) HEATING USING ELECTROCHEMICAL POWER SOURCE

(71) Applicant: L3 Open Water Power, Inc., Somerville, MA (US)

(72) Inventors: Thomas Bradford Milnes, Beverly, MA (US); Ian Salmon McKay, Seattle, WA (US); Jeffrey Michael Smith, Pembroke, MA (US); David Harvie Porter, Somerville, MA (US)

(73) Assignee: L3Harris Open Water Power, Inc., Somerville, MA (US)

( * ) Notice: Subject to any disclaimer, the term of this patent is extended or adjusted under 35 U.S.C. 154(b) by 1314 days.

(21) Appl. No.: 16/484,752

(22) PCT Filed: Mar. 7, 2018

(86) PCT No.: PCT/US2018/021413
§ 371 (c)(1),
(2) Date: Aug. 8, 2019

(87) PCT Pub. No.: WO2018/165342
PCT Pub. Date: Sep. 13, 2018

(65) Prior Publication Data
US 2019/0365563 A1    Dec. 5, 2019

Related U.S. Application Data

(60) Provisional application No. 62/468,344, filed on Mar. 7, 2017.

(51) Int. Cl.
A61F 7/03      (2006.01)
A61F 7/00      (2006.01)
H01M 8/04007   (2016.01)

(52) U.S. Cl.
CPC ........... *A61F 7/03* (2013.01); *H01M 8/04007* (2013.01); *A61F 2007/0001* (2013.01)

(58) Field of Classification Search
CPC .. F16K 35/025; A61F 7/03; A61F 2007/0001; H01M 8/04007
USPC ............................ 429/51; 126/204, 263.05
See application file for complete search history.

(56) References Cited

U.S. PATENT DOCUMENTS

| | | |
|---|---|---|
| 3,884,216 A | 5/1975 | McCartney |
| 4,150,197 A | 4/1979 | Zaromb |
| 4,430,988 A * | 2/1984 | Krasberg ............. A62B 17/005 |
| | | 126/263.02 |
| 5,376,471 A * | 12/1994 | Hunter ................... H01M 6/50 |
| | | 429/81 |

(Continued)

OTHER PUBLICATIONS

International search report for PCT/US2018/021413, dated May 31, 2018, 2 pages.

(Continued)

*Primary Examiner* — Vivek K Shirsat
(74) *Attorney, Agent, or Firm* — Danielson Legal LLC (57) ABSTRACT

A thermal management system and a method of heating a water-surface load or sub-water load. The system includes an electrochemical power source which generates electrical power and heat as a byproduct or coproduct. The electrolyte contained in the electrochemical power source is configured to transport the heat that is generated by the electrochemical power source to at least one water-surface load or sub-water load.

16 Claims, 4 Drawing Sheets

(56) References Cited

U.S. PATENT DOCUMENTS

| | | | | |
|---|---|---|---|---|
| 2010/0175862 A1* | 7/2010 | Franklin | ............... | F28D 9/0093 |
| | | | | 165/175 |
| 2012/0321920 A1* | 12/2012 | Perry | ................ | H01M 8/04276 |
| | | | | 429/70 |
| 2014/0154595 A1* | 6/2014 | McKay | ................ | H01M 12/08 |
| | | | | 429/454 |

OTHER PUBLICATIONS

Written opinion of the ISA for PCT/US2018/021413, dated May 31, 2018, 5 pages.

\* cited by examiner

HEATING USING ELECTROCHEMICAL POWER SOURCE

CROSS REFERENCE TO RELATED APPLICATIONS

The present application is a national phase application of International (PCT) Patent Appl. No. PCT/US2018/021413, filed internationally on Mar. 7, 2018, and claims the benefit of and priority to U.S. Provisional Appl. No. 62/468,344, filed on Mar. 7, 2017, the entire disclosure of each of which is incorporated by reference as if set forth in their entirety herein.

TECHNICAL FIELD

Embodiments of the invention relate generally to a method and a system for heating a water-surface or sub-water load, and more specifically to methods and systems for heating a load with heat from an electrochemical power source.

BACKGROUND

Many underwater and water-surface applications require a heat source for equipment such as diving suits, heating compartments, or the like. There is an array of heating solutions available, such as using an electric heater; a fueled heater; a reactor system; consuming a chemical feedstock in an exothermic reaction; and using the enthalpy associated with a phase change. However, these existing techniques require energy expenditure and storage space for chemicals, heaters, and other associated equipment.

Electrochemical fuel cells and batteries (hereinafter collectively referred to as "electrochemical power sources") can generate a significant amount of waste heat as a byproduct or coproduct of electrical power generation. For example, applications using an aluminum-water fuel cell can produce around two watts of heat for every watt of electrical power generated. The amount of heat created can vary depending on the amount of electrical power as well as the efficiency of the system.

Other known processes for generating heat that are based on, for example, aluminum-sodium hydroxide reactors, cupric chloride-aluminum reactors, phosphorous tri-chloride mixing systems, chemical pack heaters, or thermosensitive hydrogels do not directly generate electricity. Another one of these existing techniques relies on mixing an acid and a base to generate heat. However, this technique also only produces heat and does not produce electricity. Accordingly, existing techniques are generally directed towards either generating power or generating heat, but not both from the same process.

SUMMARY

This summary is provided to introduce a selection of concepts in a simplified form that are further described below in the Detailed Description. This summary is not meant or intended to identify or exclude key features or essential features of the claimed subject matter, nor is it intended to be used as an aid in determining the scope of the claimed subject matter.

In one aspect, embodiments relate to a thermal management system. The system comprises an electrochemical power source configured to simultaneously generate electrical power and generate heat as a byproduct or coproduct, wherein the electrochemical power source contains an electrolyte; and the electrolyte configured to transport the heat that is generated by the electrochemical power source to at least one water-surface load or sub-water load.

In one embodiment, the system further includes a pump device to assist in transporting the electrolyte to the at least one water-surface load or sub-water load.

In another embodiment, the system further includes a heat exchanger in communication with the electrochemical power source and the water-surface load or sub-water load. In further embodiments of the invention, the head exchanger includes a first channel configured to receive the heat from the electrolyte and a second channel proximate to the first channel, wherein the second channel contains a fluid, such that the heat received from the electrolyte can transfer to the fluid in the second channel. In further embodiments, the fluid is directed to the water-surface load or sub-water load. In other embodiments, the system further includes a pump device to at least assist in transporting the fluid to the water surface load or sub-water load.

In another embodiment, the heat is transported by direct conduction.

In another embodiment, the electrolyte contains charge-transporting positive ions and negative ions, the positive ions are selected from the group consisting of $H^+$, $Li^+$, $Na^+$, $K^+$, $Rb^+$, $Cs^+$, $Fr^+$, $Be^{2+}$, $Mg^{2+}$, $Ca^{2+}$, $Ba^{2+}$, and $Sr^{2+}$; and the negative ions are selected from the group consisting of: $F^-$, $Cl^-$, $Br^-$, $I^-$, $OH^-$, $NO_3^-$, $CO_3^{2-}$, $SO_4^{2-}$, and $PO_4^{3-}$.

In another embodiment, the system further includes aluminum plates configured to transport heat from the electrochemical power source to the water surface load or sub-water load by direct conduction.

In another embodiment, the electrochemical power source is suspended in a compartment adjacent to the at least one water surface load or sub-water load.

In another embodiment of the invention, the system further includes transport wires configured to transport the electrochemical power that is generated by the electrochemical power source.

In another embodiment of the invention, the water-surface load or sub-water load is a diver suit.

In another embodiment of the invention, the electrochemical power source includes at least one aluminum-water fuel cell.

In another aspect, embodiments relate to a method of heating a water-surface load or sub-water load. In embodiments of the invention, the method includes generating electricity via an electrochemical power source, wherein the electrochemical power source contains an electrolyte; simultaneously generating heat, via the electrochemical power source, as a byproduct or coproduct; and transporting the heat to at least one sub-water load or water-surface load via the electrolyte.

In one embodiment, the electrolyte used in the method is a liquid electrolyte.

In another embodiment of the method, the heat is transported to the at least one sub-water load or water surface load via a pump device.

In another embodiment, the method further includes transporting the heat to a heat exchanger in communication with the electrochemical power source and the at least one water surface load or sub-water load.

In another embodiment, the heat exchanger includes a first channel configured to receive heat from the electrolyte; and a second channel proximate to the first channel, wherein the second channel contains a fluid, such that the heat received from the electrolyte can transfer to the fluid in the second channel.

In another embodiment, the heat is transported to the water surface load or the sub-water load, at least in part, via radiation.

In another embodiment, the method further includes directing the fluid to the at least one sub-water load or water surface load.

In another embodiment of the method, the electrolyte is an aqueous electrolyte containing charge-transporting positive ions and negative ions; the positive ions are selected from the group consisting of Li$^+$, Na$^+$, K$^+$, Rb$^+$, Cs$^+$, Fr$^+$, Be$^{2+}$, Mg$^{2+}$, Ca$^{2+}$, Ba$^{2+}$, and Sr$^{2+}$ and the negative ions are selected from the group consisting of: F$^-$, Cl$^-$, Br$^-$, I$^-$, OH$^-$, NO$_3^-$, CO$_3^{2-}$, SO$_4^{2-}$, and PO$_4^{3-}$.

In another embodiment of the invention, the electrochemical power source is suspended in a compartment adjacent to the at least one water-surface load or sub-water load.

In another embodiment, the heat is transported to the water-surface load or sub-water load via convection.

In yet another aspect, embodiments relate to a method of heating a water-surface load or sub-water load. In embodiments of the invention, the method includes generating electricity via an electrochemical power source, wherein the electrochemical power source contains an electrolyte; simultaneously generating heat, via the electrochemical power source, as a byproduct or coproduct; sensing the temperature of at least one sub-water load or water-surface load via the electrolyte; and transporting the heat to the at least one sub-water load or water-surface load when the temperature of the at least one sub-water load or water-surface load is between a pre-determined temperature range.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The accompanying figures are schematic and not intended to be drawn to scale. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

The present application therefore describes a thermal management system and method that uses excess heat generated as a byproduct or coproduct of power generated by an electrochemical power source. Systems and methods of the present invention may use this excess heat to heat compartments, diver suits, or other equipment or loads in the sub-water or water-surface space. In some embodiments of the invention, the excess heat is used to heat loads in salt water environments, such as sea or ocean water. In other embodiments, the excess heat is used to heat loads in brackish water environments, such as bay water. In further embodiments of the invention, the excess heat is used to heat loads in freshwater environments, such as lakes and rivers. In other embodiments, the excess heat is used to heat loads in man-made water environments.

Thermal management systems and methods in accordance with the present invention may therefore utilize the energy output of electrochemical power sources to co-generate power and heat space-constrained vehicles or other types of loads. Instead of venting this excess heat into the environment, excess heat can be employed in a thermal management system as a heat source. Systems and methods of the present invention therefore save resources and/or enable new mission profiles. In certain embodiments of the invention, thermal management systems can preferentially heat a load and vent excess heat into the environment. This preference can be automatically determined or manually determined by a user in accordance with certain embodiments of the invention.

Additionally, thermal management systems and methods in accordance with the present invention may utilize the electrolyte in the electrochemical power source to heat space-constrained-vehicles or other types of loads by directing the electrolyte outside of the power source. In embodiments of the invention, systems and methods of the present invention therefore may use an internal electrolyte as a means of heat transportation, rather than an external fluid.

One non-limiting example of an electrochemical power source in accordance with the present invention is an aluminum-water fuel cell. In this embodiment, the aluminum reaction is exothermic and its performance can be tuned by increasing or decreasing the temperature of the cells. Accordingly, methods and systems in these embodiments may further include a temperature sensor and a mechanism for controlling the cell's temperature.

Heat in excess of what is desired to maintain these optimal operating conditions can be allocated to the load through the thermal management system. The load(s) may be, for example, compartments in a vehicle, pieces of equipment, diver suits, or a combination of the above. Additionally or alternatively, the reaction can be run at different operating conditions to increase or decrease the heat provided to the load.

More specifically, in aluminum-water fuel cells, the aluminum anode is reacted exothermically with an alkaline electrolyte to produce an electric current. Because the reaction is confined in the narrow channel between the anode and the cathode, heat may be absorbed by any of the internal cell components, the outer cell housing, and the circulating electrolyte. The load may therefore draw heat from the outer housing of the electrochemical power source, the aluminum anode, and/or the circulating electrolyte.

Accordingly, the system may provide heat to the load passively, actively, or through a combination of the two. A passive thermal management system may include a system in which the electrochemical power sources (e.g., cells) are suspended in a compartment adjacent to the load. In these types of passive embodiments, heat may transfer via convection and/or radiation from the compartment housings. Embodiments using radiation to transfer heat rely on electromagnetic waves to carry heat. Embodiments using convection to transfer heat rely on the movement of particles of gasses or liquids, such as an electrolyte or a second working fluid, to transfer heat. Embodiments may rely on both radiation and convection to transfer heat from the electrochemical power source to the load or heat exchanger.

For example, the electrolyte may be kept within the compartment housing to heat the housing, and the housing may then provide heat to the external load via radiation. In another passive embodiment, the load may be placed in direct contact with the compartment housings so that the heat is conductively transferred.

Active thermal management systems may include those in which the electrolyte is used as a working fluid or a separate working fluid is employed with a heat exchanger. In both cases, the working fluid could be run through a radiator or connected to a diver suit or other type of load via one or more channels. For example, in certain embodiments of the invention, the electrolyte or a separate working fluid may be directed to a cell attached to a vehicle or other chamber. This chamber may be submerged under water or it may be on the surface of the water. The cell attached to the chamber, in certain embodiments, may be configured to allow the fluid or electrolyte to flow through the cell. In so doing, the fluid or electrolyte may radiate heat into the cell. In certain embodiments, the cell may be optimized such that the cell may radiate more heat into the chamber than into the surrounding environment. In other embodiments of the invention, the system may also use a waste management system. In some embodiments, the waste management system may at least assist in controlling the temperature of at least one of the electrolyte, a separate working fluid, or the chamber. In further embodiments of the invention, the temperature of the chamber may be manually or automatically controlled. Other embodiments of the invention may have a safety mechanism to automatically stop the circulation of fluid or start the circulation of fluid if the chamber reaches a certain temperature. For example, if the temperature of the chamber reaches above 30° C., in certain embodiments of the invention, a safety mechanism will automatically stop the flow of electrolyte or fluid into the cell. This cessation will lead, in certain embodiments, to at least a cessation of heat radiating into the chamber and, in other embodiments, a cooling of the chamber.

In one embodiment, the electrolyte may be aqueous potassium hydroxide (i.e., an aqueous solution including potassium hydroxide). The type of electrolyte used and the pH of said electrolyte may of course vary and may depend on the specific type of cell. For example, in other embodiments the electrolyte may be aqueous sodium hydroxide, aqueous lithium hydroxide, aqueous potassium hydroxide, water, or the like. In other embodiments of the invention, the electrolyte contains a number of charge-transporting positive and negative ions. In certain embodiments of the invention, the positive ions may be selected from any of the alkali metals or alkaline metals. In other embodiments of the invention, the positive ions are selected from the group consisting of $H^+$, $Li^+$, $Na^+$, $K^+$, $Rb^+$, $Cs^+$, $Fr^+$, $Be^{2+}$, $Mg^{2+}$, $Ca^{2+}$, $Ba^{2+}$, and $Sr^{2+}$.

In other embodiments of the invention, the negative ions may be selected from any of the halogens. In other embodiments, the negative ions are selected from the group consisting of: $F^-$, $Cl^-$, $Br^-$, $I^-$, $OH^-$, $NO_3^-$, $CO_3^{2-}$, $SO_4^{2-}$, and $PO_4^{3-}$.

The circulating electrolyte of the aluminum-water electrochemical power source can be used as a working fluid in a heat exchanger scheme. Or, the circulating electrolyte may be transported to a second heat exchanger using a secondary working fluid. Thus, excess heat may be transferred to the equipment, compartment, diver suit, or other type of load directly or indirectly.

In some embodiments, a pump device may at least assist in transporting the electrolyte to heat the load or to a heat exchanger. In other embodiments, a second pump device may at least assist in transporting air or another fluid on or over the load to improve heat transfer to the load. In embodiments wherein a pump or other controlled driving force moves at least one of the electrolyte or the second working fluid, the heat is transported by the electrolyte or second working fluid to the load or a heat exchanger via forced convection. However, a pump is not necessarily required for heat transportation and, for example, the electrolyte may be static and heat the load by conduction natural convection and/or radiation. In this type of embodiment, conduction and convection heating will generally be more dominant than radiation, especially in moderate temperature ranges.

Figure 1:
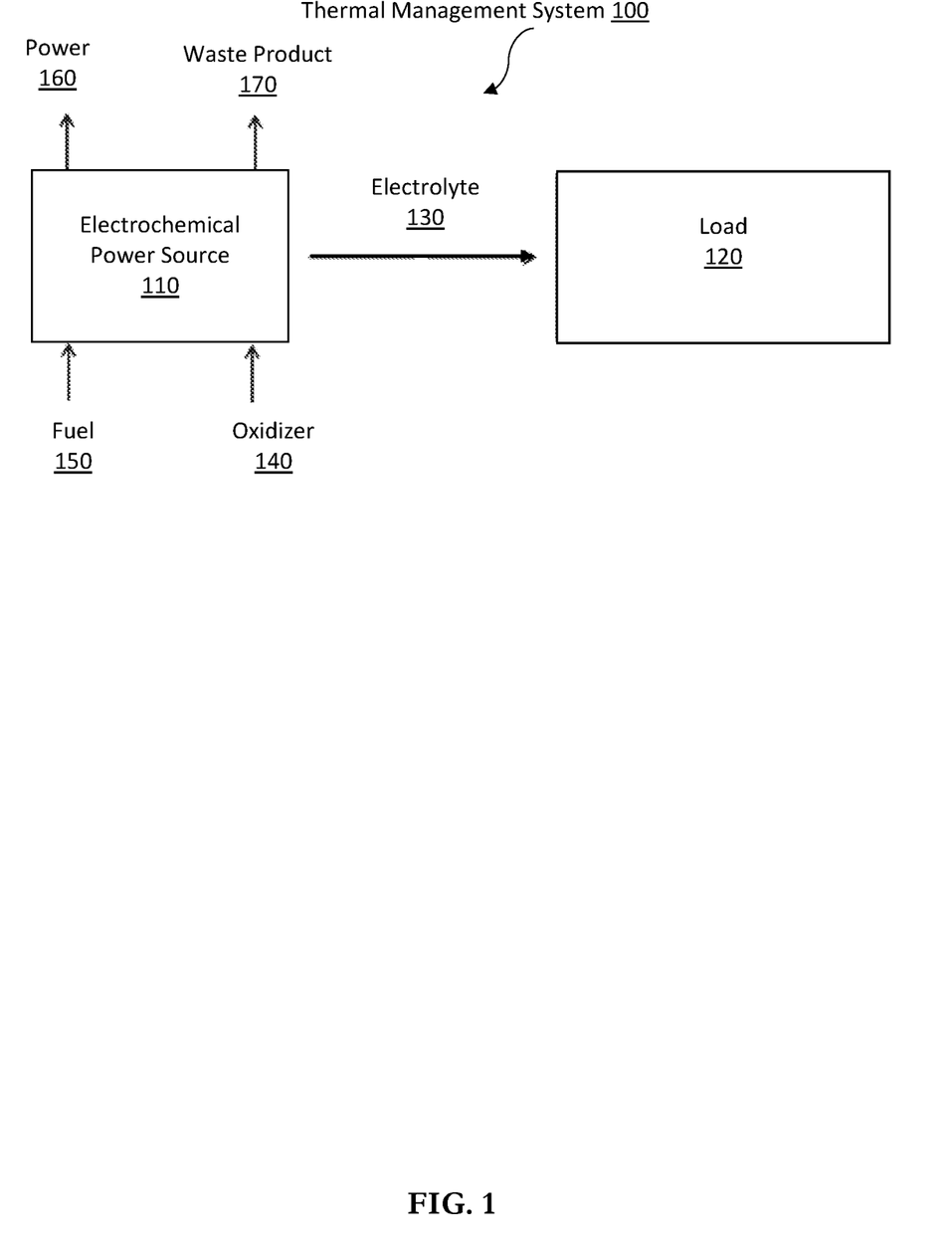
FIG. 1 illustrates a block diagram illustrating an electrolyte having excess thermal heat being transported from an electrochemical power source and being directly applied in a thermal management system in accordance with one embodiment.

FIG. 1 illustrates a thermal management system 100 in accordance with embodiments of the invention. In embodiments of the invention, a fuel 150 and an oxidizer 140 may be used by the electrochemical power source 110 to generate power 160. In embodiments of the invention, the electrochemical power source 110 is an electrochemical cell. In embodiments of the invention, waste product 170 may also be generated. In some embodiments, hydrogen is used as a fuel 150 for the electrochemical power source 110.

In embodiments of the invention, the electrolyte 130 from the electrochemical power source 110 may be circulated from the electrochemical power source 110 to the load 120. The electrolyte 130 may contain heat generated from the electrochemical power source 110. In embodiments of the invention, the heated electrolyte 130 may be directed to heat an entire load 120 or part of the load 120. After the electrolyte 130 is circulated around the load 120, in certain embodiments, the electrolyte 130 is directed back to the electrochemical power source 110 and reheated in the electrochemical power source 110. Then, in certain embodiments, the electrolyte 130 may be recirculated. Embodiments using the electrolyte 130 externally by directing the electrolyte 130 to the load 120 may be more efficient than embodiments which rely on convection or radiation to heat the load 120. In the embodiments which direct the electrolyte 130 to the load 120, the electrolyte 130 may be considered a working fluid.

In certain embodiments of the invention, the electrochemical power source 110 may produce approximately 2 watts of heat per watt of power 160. In other embodiments, the electrochemical power source 110 may produce approximately 1 watt of heat per one watt of electrical power. In further embodiments, including embodiments operating at different efficiency levels or operating with alloys having low coulombic efficiencies, the electrochemical power source 110 may produce 5 or more watts of heat per one watt of electrical power. In certain embodiments, the electrochemical power source 110 may be controlled to run at a different voltage to increase the amount of heat generated per unit of power 160. In other embodiments of the invention, the electrochemical power source 110 may be run to produce more power 160 and less heat. The switch from a high heat-producing mode to a high-power low-heat producing mode may be automatic or manual. Certain embodiments of the invention may employ a cell management board to control the output of the electrochemical power source 110. A user may choose certain embodiments of the system using an electrochemical power source 110 which produces a greater ratio of watts of heat per watt of electrical power, such that the system produces a greater amount of heat to be used in thermal management capacities.

In some embodiments of the invention, heat is transferred via direct conduction. In some of these embodiments, the heat may be transferred via the boundary between the electrochemical power source 110 and the load 120. In some embodiments, this boundary is comprised of aluminum plates. In certain embodiments, the electrochemical power source 110 is suspended in a compartment adjacent to the at least one water-surface load or sub-water load 120.

Figure 2:
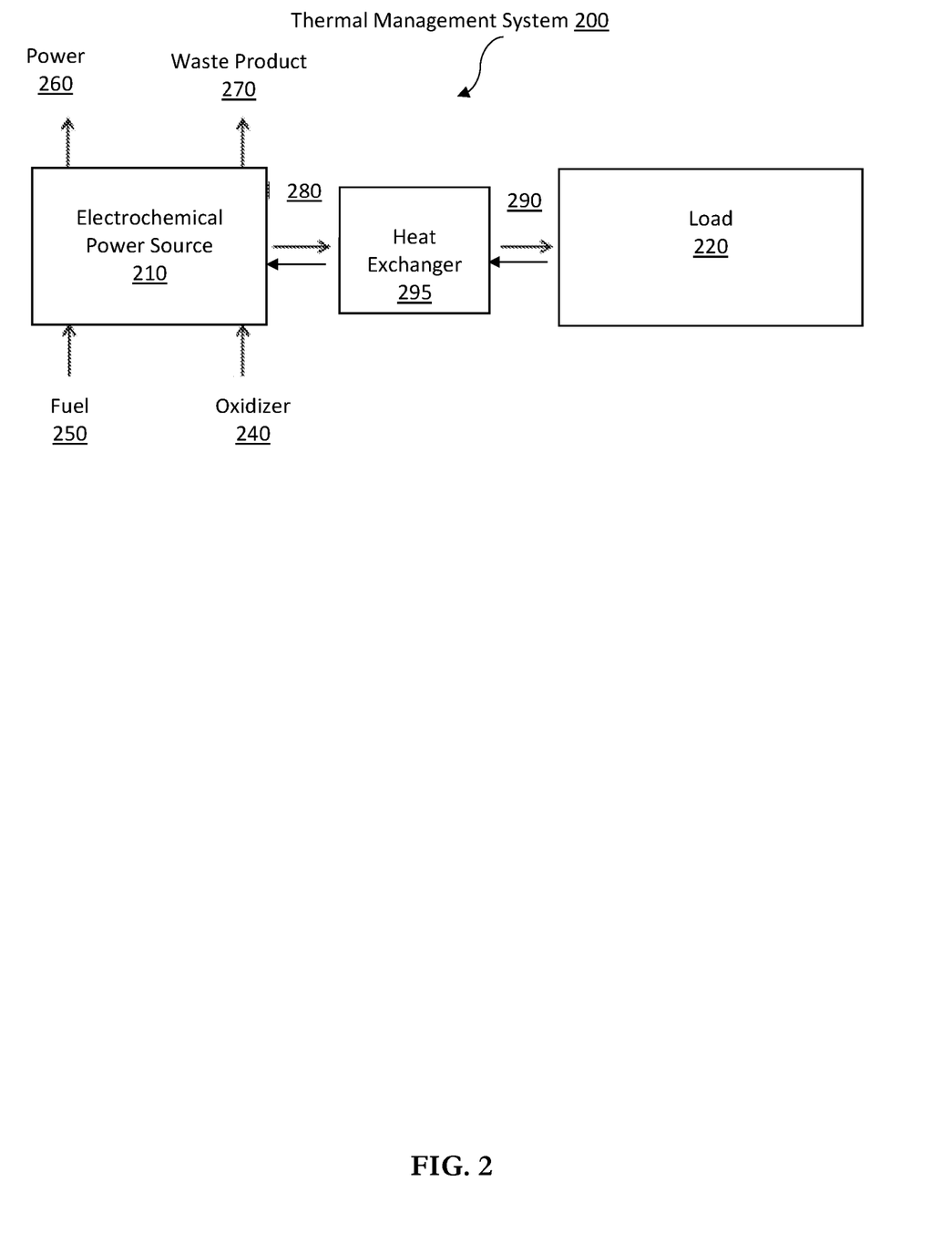
FIG. 2 illustrates a block diagram illustrating excess thermal heat from an electrochemical power source being indirectly applied in a thermal management system through a heat exchanger in accordance with one embodiment.

FIG. 2 illustrates a thermal management system 200 in accordance with embodiments of the present invention. In embodiments of the invention, a fuel 250 and an oxidizer 240 may be used by the electrochemical power source 210 to generate power 260. In embodiments of the invention, the electrochemical power source 210 is an electrochemical cell. In embodiments of the invention, waste product 270 may also be generated. In certain embodiments of the invention, a waste management system is employed to remove the waste product 270 from the system 200. This is further illustrated in FIG. 3. In embodiments of the invention as shown in FIG. 2, concentrated or otherwise toxic electrolytes may not be directly circulated to a load 220. In some embodiments, this is due to safety concerns. The indirect thermal management system, as illustrated in FIG. 2, uses a heat exchanger 295 to convert the heat generated in the electrochemical power source 210 into usable heat 290 to control the temperature of the load 220. For applications in which safety concerns take precedence, the indirect thermal management system 220 may be preferred despite requiring the addition of a heat exchanger 295.

In embodiments of the invention, the heat exchanger 295 contains a working fluid 290 that can be circulated around the load 220. In embodiments of the invention, the electrochemical power source 210 increases the temperature of the electrolyte 280 contained within the electrochemical power source 210. After the electrolyte 280 is heated, the electrolyte 280 from the electrochemical power source 210 is directed to a heat exchanger 295 in certain embodiments of the invention. In embodiments of the invention, the heat exchanger 295 allows the heat from the electrolyte 280 to pass to a working fluid 290 without mixing the electrolyte 280 from the electrochemical power source 210 and the working fluid 290. In embodiments of the invention, the working fluid 290 is heated by the electrolyte 280 in the heat exchanger 295 and then directed to the load 220.

In embodiments of the invention, after the electrolyte 280 is circulated through the heat exchanger 295, the electrolyte 280 is circulated back to the electrochemical power source 210 to be heated again. In embodiments of the invention, the electrolyte 280 is directed to the heat exchanger 295 and the electrochemical power source 210 via pump. Some embodiments of the invention may use positive displacement pumps, including rotary-type pumps, reciprocating-type pumps, and linear-type pumps. Further embodiments can use diaphragm pumps and peristaltic pumps. Other embodiments use gravity and gravity-fed pumps to transport the fluid or electrolyte around the system. Further embodiments reply on diaphragm pumps and static pumps to transport the fluid and electrolyte.

In some embodiments, positive displacement pumps can produce the same flow of fluid at a given speed regardless of discharge pressure, which creates a constant flow. Some embodiments may employ a relief or safety valve to stop the flow of fluid.

In embodiments of the invention, the working fluid 290 can be chosen to be compatible with the load 220. In certain embodiments where the load 220 is a diving suit, the working fluid 290 can be chosen to be compatible with existing diving suit designs. For example, in suits that are already designed to circulate water, the working fluid 290 circulating through the heat exchanger 295 could be purified water or seawater. It is important to note that these diving suits are largely independent of the heat source themselves and instead take a heated stream as an input. Other embodiments, for example, may use heated air as a working fluid or materials that undergo a phase change and could be recharged by the heat generated by an electrochemical cell.

In embodiments of the invention, after the heated working fluid 290 is circulated around the load 220, the working fluid 290 is recirculated to the heat exchanger 295. The working fluid 290 is reheated in the heat exchanger 295 with the heat from the electrolyte 280 directed from the electrochemical power source 210. In a similar fashion, in certain embodiments of the invention, the electrolyte 280 is circulated from the electrochemical power source 210 to the heat exchanger 295 and then, after circulating through the heat exchanger 295, the electrolyte is redirected to the electrochemical power source 210.

In embodiments of the invention, the electrolyte 280 is returned to the electrochemical power source 210 at a different temperature than when the electrolyte 280 left the electrochemical power source 210. In embodiments of the invention, the electrolyte 280 is cooler when it returns to the electrochemical power source 210 than when it first left the electrochemical power source 210 and began to circulate to the heat exchanger 295. In embodiments, the working fluid 290 returns to the heat exchanger 295 at a different temperature than when the working fluid 290 left the heat exchanger 295. In certain embodiments, the working fluid 290 is cooler when it returns to the heat exchanger 295 than when it first left the heat exchanger 295. In embodiments of the invention, the working fluid 290 is hottest when it is present inside the heat exchanger 295. In embodiments of the invention, the electrolyte 280 is hottest when it is present inside the electrochemical power source 210.

In certain embodiments of the invention, the heating and circulation of the working fluid 290 and electrolyte 280 is continuous. In other embodiments of the invention, a user can control the circulation of the working fluid 290 and the electrolyte 280 in the thermal management system 200 with a switch. In other embodiments of the invention, a temperature regulator is used to automatically regulate at least one of the temperature of the load 220, the temperature of the electrolyte 280, and the temperature of the working fluid 290. In some embodiments of the invention, the temperature regulator is disposed on the load 220. In other embodiments of the invention, the temperature regulator is disposed on the electrochemical power source 210.

In embodiments of the invention, the electrolyte 280 may have the same composition make-up as the working fluid 290. In other embodiments of the invention, the electrolyte 280 has a different composition than the working fluid 290. In other embodiments, the electrolyte 280 and the working fluid 290 may have the same chemical composition, but the electrolyte 280 and the working fluid 290 may be present in different phases in the system. For example, in certain embodiments, the electrolyte 280 may be present in the system as a liquid and the working fluid 290 may be present as a gas. Some embodiments of the invention may use water, glycols, water-glycol mixtures, hydrofluorocarbons, or chlorofluorocarbons as a working fluid 290. Other embodiments of the invention may use steam or ethylene glycol as a working fluid 290. The above working fluids should only be construed as exemplary and non-limiting types of working fluids in certain embodiments of the present invention.

In embodiments of the invention, the heat from the electrochemical power source 210 may be transferred to the load 220 via convection or radiation. In a convection model, in accordance with certain embodiments, the electrolyte 280 may carry heat along with the flow of the electrolyte 280. This process may also move heat partly by diffusion as well. In some embodiments, the electrolyte 280 and the second working fluid 290 may transfer heat through forced convection, wherein the electrolyte 280 and second working fluid 290 may flow by use of a pump or fan. Other embodiments may use gravitational fields, wherein the electrolyte 280, the second working fluid 290, or both may expand through increased thermal energy and flow through the thermal management system 200 to transfer heat.

Figure 3:
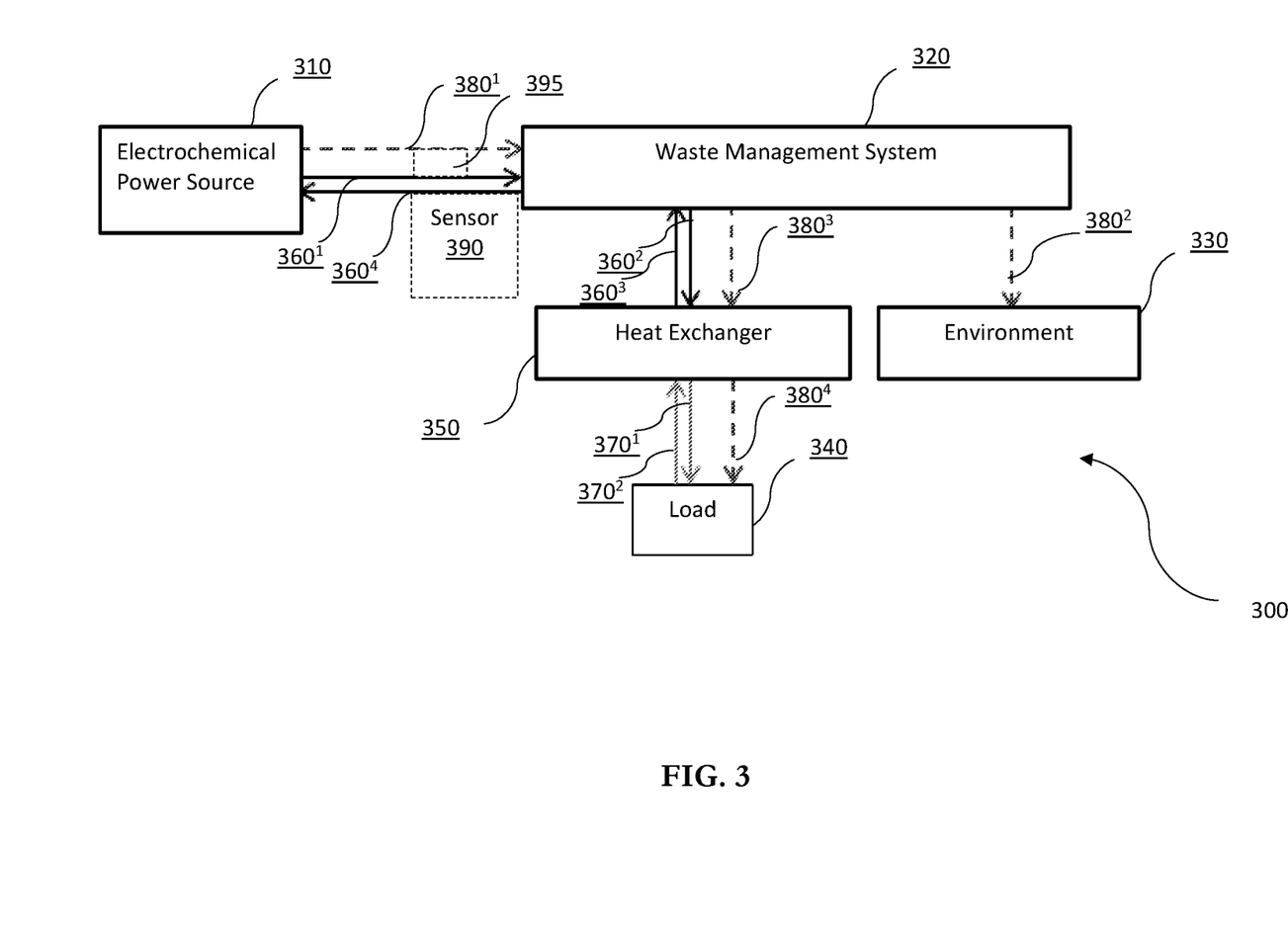
FIG. 3 illustrates a block diagram illustrating a thermal management system for directing heat from an electrochemical power source to a load, wherein the system further contains a waste management system.

FIG. 3 illustrates a thermal management system 300 having a waste management system 320 in accordance with certain embodiments of the present invention. In addition to embodiments of the waste management system 320 described below, embodiments of the invention may use a waste management system as illustrated and described in U.S. patent application Ser. No. 15/713,617, the entire disclosure of which is hereby incorporated by reference in its entirety. In certain embodiments, an electrolyte 360 may flow from the electrochemical power source 310 to a heat exchanger 350. The electrolyte $360^1$ may be directed from the electrochemical power source to the waste management system 320. After passing through the waste management system 320, in certain embodiments, the electrolyte $360^2$ may continue to be directed to a heat exchanger 350. After the electrolyte is circulated through the heat exchanger 350, the electrolyte may be directed back $360^3$ through the waste management system 320 and back $360^4$ to the electrochemical power source 310.

In embodiments of the invention, the electrolyte 360 transports heat $380^1$ from the electrochemical power source 310 and through the waste management system 320 toward $380^3$ the heat exchanger 350. In certain embodiments, a second working fluid 370 may flow $370^1$ from the heat exchanger 350 toward the load 340. Once the second working fluid 370 circulates around the load 340, in certain embodiments, the second working fluid 370 may flow $370^2$ back to the heat exchanger 350.

In some embodiments, the heat exchanger 350 is not present and the electrolyte $360^2$ may flow directly to the load 340.

In some embodiments, at least one of the electrolyte and the second working fluid 370 may be directed through the thermal management system 300 via pumps.

Similar to the system described above and depicted in FIG. 2, in embodiments of the invention, the heat exchanger 350 contains the working fluid 370 that can be circulated around the load 340. In embodiments of the invention, the electrolyte transports heat $380^1$ from the electrochemical power source 310 through the waste management system 320 and then transports the heat $380^3$ to the heat exchanger 350. The heat 380 as transported by the electrolyte 360 heats the second working fluid 370 in the heat exchanger 350. Then, in accordance with certain embodiments of the invention, the second working fluid 370 transports the heat $380^4$ to the load 340.

Certain embodiments of the invention use a waste management system 320 to prolong the life of the electrochemical power source 310, such as a fuel cell. In certain embodiments of the invention, waste may form on the anode in the electrochemical power source 310. In embodiments, the waste may precipitate out into the electrolyte 360. This waste may be removed from the electrolyte 360 by using filters in the waste management system 320. In some embodiments, each cell within the electrochemical power source 310 may have a separate waste removal system 320 or many cells may share a waste removal system 320. In embodiments where the electrolyte waste is allowed to build up in the electrochemical power source 310, the electrolyte 360 or the electrochemical power source 310 or both may be replaced periodically.

In an exemplary embodiment of a thermal management system 300 containing a waste management system 320, the anode in the electrochemical power source 310 may be composed of aluminum or an aluminum alloy. In embodiments of the invention, aluminum hydroxide forms on the anode as the thermal management system 300 runs. In certain embodiments, the aluminum hydroxide byproduct or waste may precipitate as a particulate into the electrolyte 360 or may grow in crystalline form on the anode. In certain embodiments of the system wherein the waste management system 320 is contained within the electrochemical power source 310, foam can be used to surround the anode and grow the aluminum hydroxide crystals. In other embodiments of the system, the waste management system 320 can capture particulates of aluminum hydroxide in the electrolyte as it circulates through the thermal management system 300.

In certain embodiments of the invention, the waste management system 320 is designed as a single-use module, wherein the foam or filter is used to capture all the particulates of the aluminum hydroxide and, once the aluminum hydroxide waste begins to significantly impair the performance of the thermal management system 300, the electrolyte, individual cells, or the entire electrochemical power source 310 may be cleaned or replaced. In other embodiments of the invention, the waste management system 320 may contain several sections of foam, which are inserted in a compressed state into the waste management system 320. A first section of foam 320 may expand when aluminum hydroxide attaches to the foam. When the performance of the thermal management system becomes impaired with a buildup of aluminum hydroxide, the first section of foam may be removed through bomb bay doors contained in the waste management system 320. This removal of foam may expose a second section of foam to the waste management system 320 and the second section of foam may begin to expand in a similar manner to the first section of foam. In embodiments of the invention, the foam may act as a nucleation point for waste byproduct. In embodiments of the invention, the waste management system may contain multiple sections of foam.

In certain embodiments of the invention, the waste management system is further optimized by controlling the pressure and temperature of the electrolyte 360 and the electrochemical power source 310. In embodiments of the invention, lower temperature and higher pressure of the electrolyte 360 may produce crystalline waste rather than particulate waste. In embodiments of the invention, the waste removal system may optimally work at lower temperatures to remove crystallized waste product.

In certain embodiments, the waste management system 320 is contained within the electrochemical power source 310. In other embodiments, the waste management system 320 is connected directly to the load 340. In other embodiments of the invention, the waste management system 320 is connected to the heat exchanger 350 and is not directly connected to the electrochemical power source 310.

In certain embodiments of the invention, excess heat $380^2$ in the waste management system 320 is directed to the environment 330. In certain embodiments of the invention, insulating materials are placed around at least one of the waste management system 320, the heat exchanger 350, the electrochemical power source 310, and the load 340 to prevent excess loss of heat 380. The insulating materials in the thermal management system 300 may be manually removed or added as needed.

In certain embodiments of the invention, the insulating materials used to insulate the bomb bay doors of the waste management system 320 are the same materials used to insulate the electrochemical power source 310 or individual cells within the electrochemical power source 310. In other embodiments of the invention, the insulating materials used to insulate different parts of the thermal management system 300 are different, depending on the needs of the system. In certain embodiments, insulating materials preferably have densities lower than water for improving buoyancy for certain loads, including an unmanned underwater vehicle. Certain embodiments may use a thin layer of air or vacuum between two walls to serve as insulation for at least one of the electrochemical power source 310, the waste management system 320, the heat exchanger 350, or the load 340. Other embodiments may use sprayed foams, wool, heavy fabrics, or neoprene as insulating materials for at least one of the electrochemical power source 310, the waste management system 320, the heat exchanger 350, or the load 340.

As an example, insulating materials could be polymers or syntactic foam. In certain exemplary embodiments, polypropylene, high density polyethylene, acrylonitrile butadiene styrene, or other composite materials may be used as insulating materials. In other embodiments, a combination of the above materials insulates the thermal management system 300.

In certain embodiments of the invention, the system 300 may further include a sensor 390 in direct contact with the electrolyte 360 or second working fluid 370. In certain embodiments of the invention, the sensor 390 may also be in direct contact with the electrochemical power source 310. In other embodiments of the invention, the sensor 390 may be in direct contact with the load 340. In further embodiments, the sensor 390 may be in direct contact with the heat exchanger 350 or the waste management system 320. In embodiments of the invention, a sensor 390 may be configured to remain at a temperature less than or equal to the electrolyte 360 or second working fluid 370 and greater than the environment surrounding the system 300. In other embodiments, the system could include a pump 395 to further aid in transporting at least one of the electrolyte 360 or the second working fluid 370. In certain embodiments, the pump is in contact with at least one of the electrochemical power source 310, the waste management system 320, the heat exchanger 350, or the load 340. In other embodiments, multiple pumps can be used to transport the electrolyte 360, the second working fluid 370, or both the electrolyte 360 and the second working fluid 370.

In certain embodiments of the invention, the pump 395 may be used to circulate the electrolyte 360, the second working fluid 370, or both the electrolyte 360 and the second working fluid 370. In embodiments, at least one pump 395 may be in communication with the sensor 390 and may control the speed at which the working fluid 370 or electrolyte 360 flows through the system 300. For example, if the sensor detects a temperature at which more heat must be transported, the pump 395 may pump the electrolyte 360 or the second working fluid 370 through the system 300 at a faster rate.

Figure 4:
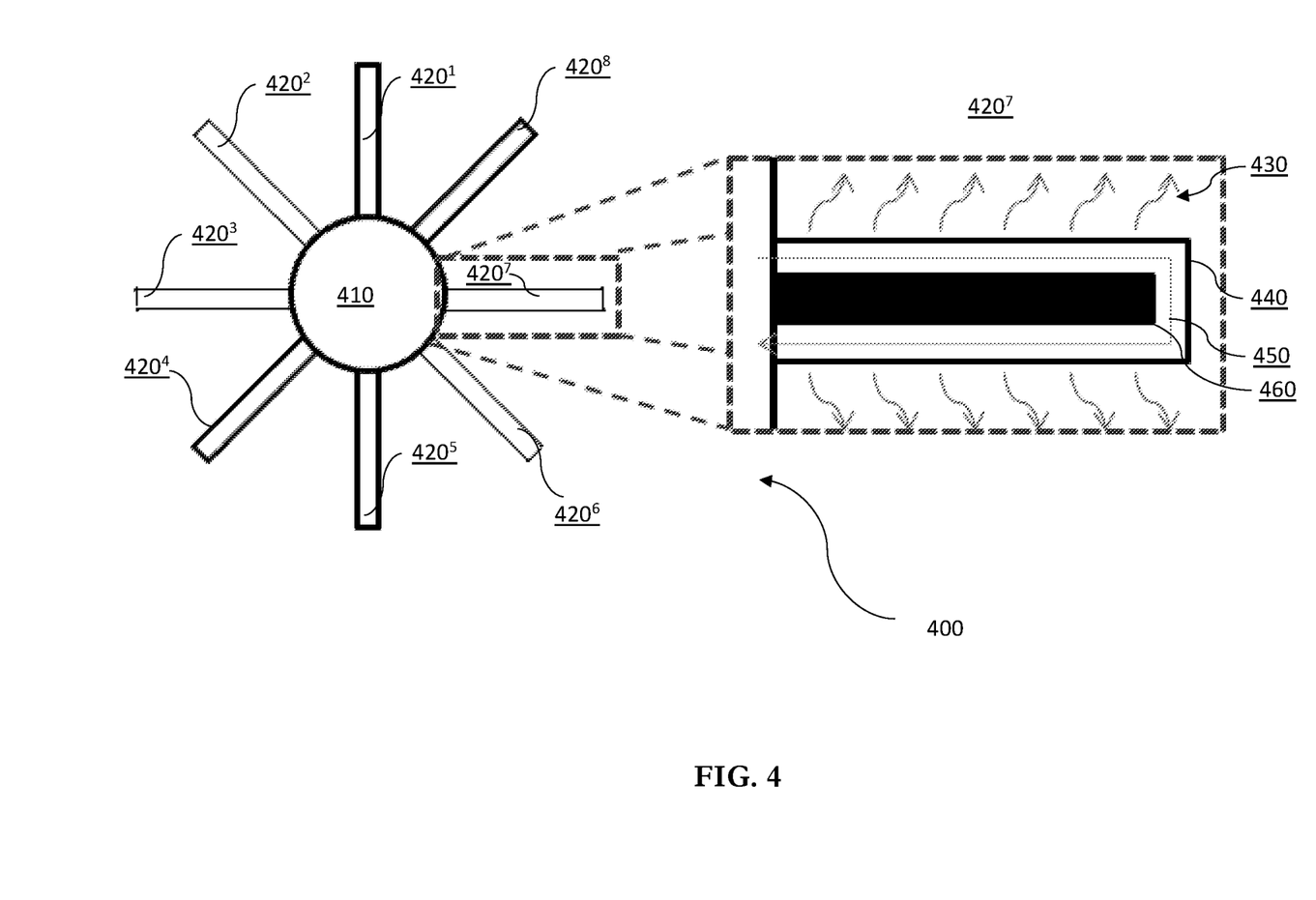
FIG. 4 illustrates a circular configuration of cells around a balance of plant used to heat a load.

FIG. 4 illustrates a cell stack 400 containing multiple cells 420 around a central balance of plant 410 for the cell stack 400, in accordance with certain embodiments of the present invention. In certain embodiments, an electrochemical power source is made of a cell stack 400 with multiple cells. A cell stack 400 may be configured in multiple ways to optimize heat transfer from the cell stack 400 to a load. In certain embodiments, each cell can be approximately 1 cm or 1.5 cm thick. In embodiments of the invention, cells 420 are placed such that there is at least 1 mm of space between one cell $420^1$ and the next cell $420^2$. In certain embodiments, cells 420 are stacked on top of each other with insulating material between each cell. In other embodiments, cells 420 are arranged in a radiator arrangement, as depicted in FIG. 4.

In certain embodiments, each individual cell 420 may have a cell housing 440 around the aluminum plate or anode 460. In certain embodiments, the cell housing 440 is made of insulating material, such as polypropylene. In certain embodiments, the electrolyte 450 may circulate in the individual cell $420^7$. In certain embodiments, the same electrolyte 450 may circulate through all cells 420 contained in the cell stack 400. In embodiments of the invention, heat 430 may radiate out from individual cells 430 or may be insulated and contained within the electrolyte 450 and directed, through the electrolyte 450 to a load or heat exchanger. In other embodiments of the invention, at least two cells $420^1$, $420^2$ may be centrally stacked in a cell stack and the electrolyte 450 may be directed radially out from the cell stack in a similar configuration to the illustration of FIG. 4. In other embodiments of the invention, the electrolyte 450 of one cell 420 may be directed radially out from the cell 420 in at least two directions to facilitate heat transfer from the cell to a load via electrolyte 450.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

What is claimed is:

1. A thermal management system, the system comprising:
an electrochemical power source configured to simultaneously generate electrical power and generate heat as a byproduct or coproduct, wherein the electrochemical power source contains an electrolyte; and
the electrolyte configured to transport the heat that is generated by the electrochemical power source to at least one water-surface load or sub-water load; and
a heat exchanger in communication with the electrochemical power source and the water-surface load or sub-water load, wherein the heat exchanger comprises:
a first channel configured to receive the electrolyte and return it to the electrochemical power source after circulating the electrolyte past a second channel, and
the second channel is proximate to the first channel, wherein the second channel contains a fluid, such that the heat from the electrolyte can transfer to the fluid in the second channel.

2. The system of claim 1, further comprising a pump device to at least assist in transporting the electrolyte to the at least one water-surface load or sub-water load.

3. The system of claim 1, further comprising a waste management system configured to remove precipitate byproduct of the electrochemical power source, wherein the waste management system comprises a porous media.

4. The system of claim 1, wherein the heat is transported by direct conduction.

5. The system of claim 4, further comprising aluminum plates configured to transport heat from the electrochemical power source to the water-surface load or sub-water load by direct conduction.

6. The system of claim 1, wherein the electrochemical power source is suspended in a compartment adjacent to the at least one water-surface load or sub-water load.

7. The system of claim 1, wherein the water-surface load or sub-water load is a diver suit.

8. The system of claim 1, wherein the electrochemical power source comprises at least one aluminum-water fuel cell.

9. The system of claim 1, wherein the heat is transported to the water-surface load or the sub-water load via at least one of radiation or convection.

10. The system of claim 1, wherein the electrochemical power source comprises:
a cell stack having at least two cells; and
a balance of plant,
wherein the cells are radially arranged around the balance of plant.

11. A method of heating a water-surface load or a sub-water load, the method comprising:
generating electricity via an electrochemical power source, wherein the electrochemical power source contains an electrolyte;
simultaneously generating heat, via the electrochemical power source, as a byproduct or coproduct; and
transporting the heat to at least one sub-water load or water-surface load via the electrolyte by using a heat exchanger in communication with the electrochemical power source and the water-surface load or sub-water load, wherein the heat exchanger comprises:
a first channel configured to receive the electrolyte and return it to the electrochemical power source after circulating the electrolyte past a second channel, and the second channel is proximate to the first channel, wherein the second channel contains a fluid, such that the heat from the electrolyte can transfer to the fluid in the second channel.

12. The method of claim 11, wherein the heat is transported to the at least one sub-water load or water surface load via a pump device.

13. The method of claim 11, further comprising directing the fluid to the at least one sub-water load or water surface load.

14. The method of claim 11, wherein the heat is transported to the water-surface load or the sub-water load via at least one of radiation or convection.

15. The method of claim 11, wherein the heat is transported to the water-surface load or the sub-water load via conduction.

16. A method of heating a water-surface load or a sub-water load, the method comprising:
  generating electricity via an electrochemical power source, wherein the electrochemical power source contains an electrolyte;
  simultaneously generating heat, via the electrochemical power source, as a byproduct or coproduct;
  sensing the temperature of at least one sub-water load or water-surface load via the electrolyte; and
  transporting the heat to the at least one sub-water load or water-surface load when the temperature of the at least one sub-water load or water-surface load is between a pre-determined temperature range by using a heat exchanger in communication with the electrochemical power source and the water-surface load or sub-water load, wherein the heat exchanger comprises:
    a first channel configured to receive the electrolyte and return it to the electrochemical power source after circulating the electrolyte past a second channel, and
    the second channel is proximate to the first channel, wherein the second channel contains a fluid, such that the heat from the electrolyte can transfer to the fluid in the second channel.

* * * * *